United States Patent [19]

Lybarger

[11] 3,947,506

[45] Mar. 30, 1976

[54] RECOVERY OF ISOPRENE

[75] Inventor: Hugh M. Lybarger, Akron, Ohio

[73] Assignee: The Goodyear Tire & Rubber Company, Akron, Ohio

[22] Filed: Apr. 3, 1974

[21] Appl. No.: 457,329

[52] U.S. Cl............................ 260/681.5 R; 203/70
[51] Int. Cl.².......................................... C07C 7/06
[58] Field of Search................. 260/681.5 R; 203/70

[56] References Cited
UNITED STATES PATENTS

| | | | |
|---|---|---|---|
| 2,614,969 | 10/1952 | Morrell et al.......................... | 203/70 |
| 3,230,157 | 1/1966 | Hill et al. ...................... | 260/681.5 R |
| 3,274,286 | 9/1966 | Reich........................... | 260/681.5 R |
| 3,439,060 | 4/1969 | Kempton..................... | 260/681.5 R |
| 3,557,239 | 1/1971 | Gebhart et al. .............. | 260/681.5 R |
| 3,692,861 | 9/1972 | Chikatsu et al. ............. | 260/681.5 R |

Primary Examiner—Paul M. Coughlan, Jr.
Attorney, Agent, or Firm—F. W. Brunner; J. Y. Clowney

[57] ABSTRACT

There is disclosed a method of recovery of isoprene from a hydrocarbon stream consisting of predominately C-5 hydrocarbons and containing isoprene, n-pentane and other 5 carbon atom hydrocarbons which comprises subjecting said hydrocarbon stream to two successive high efficiency distillations, the first distillation being conducted in a manner as to remove as an overhead fraction, hydrocarbon components of said stream which are more volatile than the azeotrope of isoprene/n-pentane and as a bottom fraction the other hydrocarbons in said stream, subjecting the bottom fraction from the first distillation to the second distillation, the second distillation being conducted in a manner as to remove the azeotrope of isoprene/n-pentane as an overhead fraction and as a bottom fraction the other hydrocarbons which are less volatile than the azeotrope of isoprene/n-pentane, and recovering the isoprene/n-pentane azeotrope.

4 Claims, 5 Drawing Figures

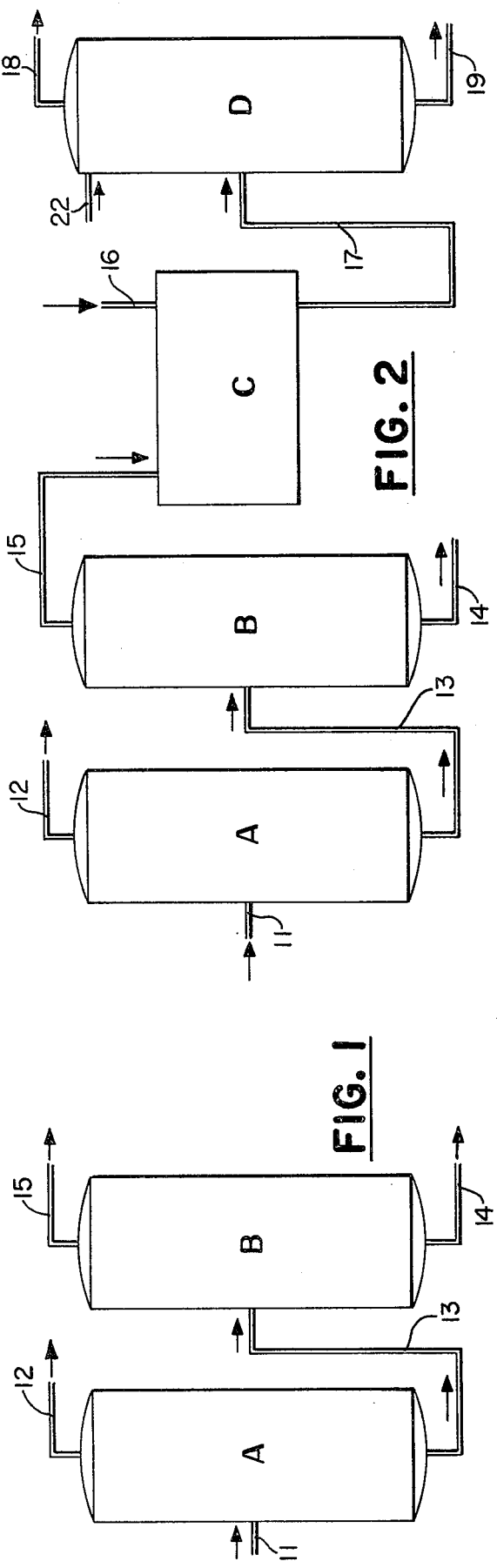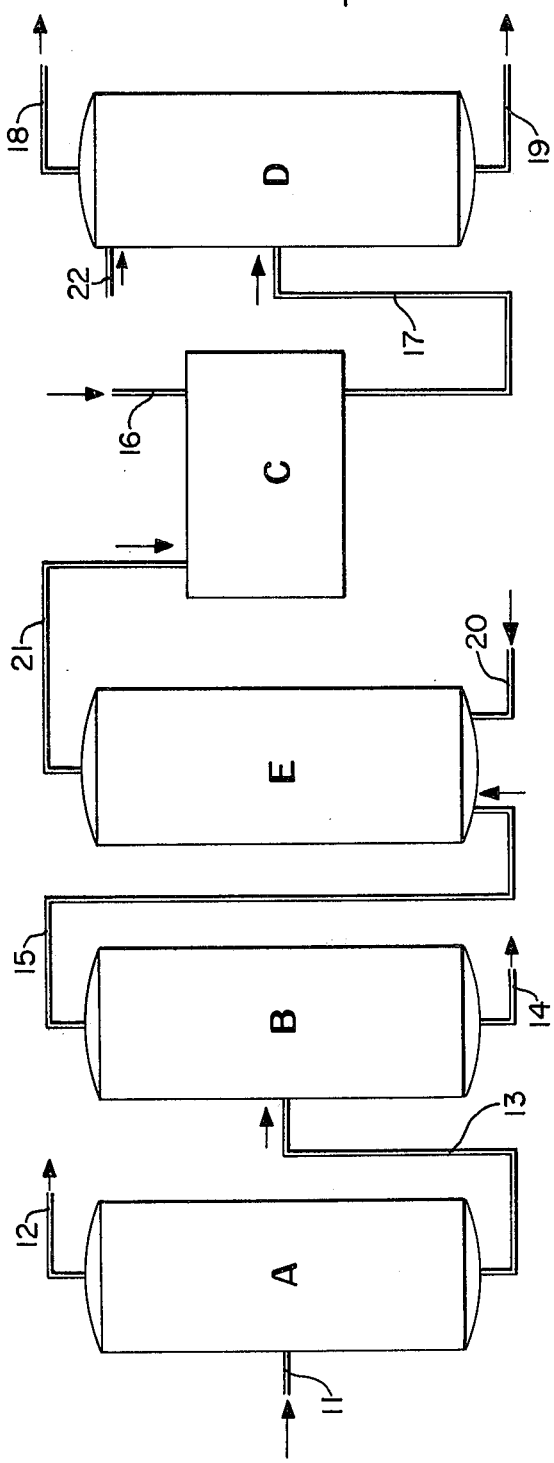

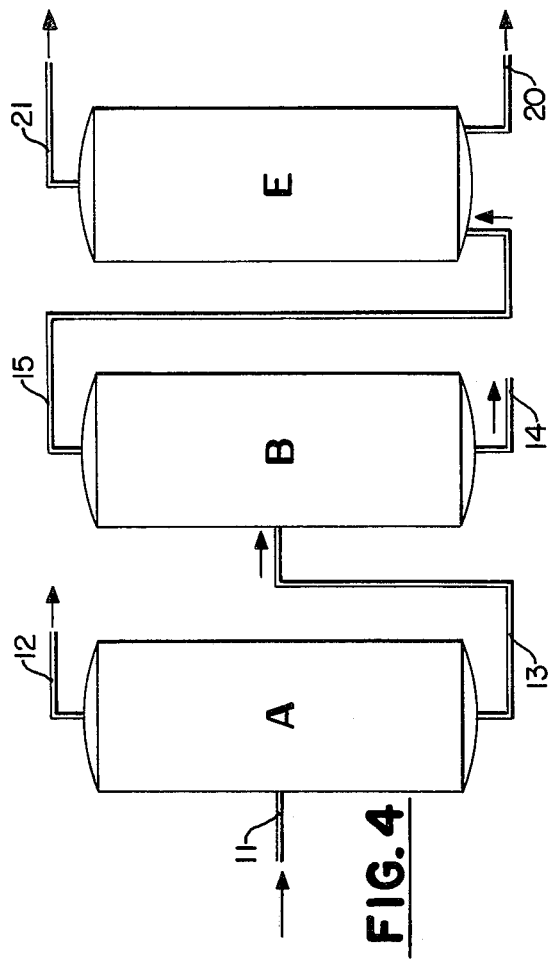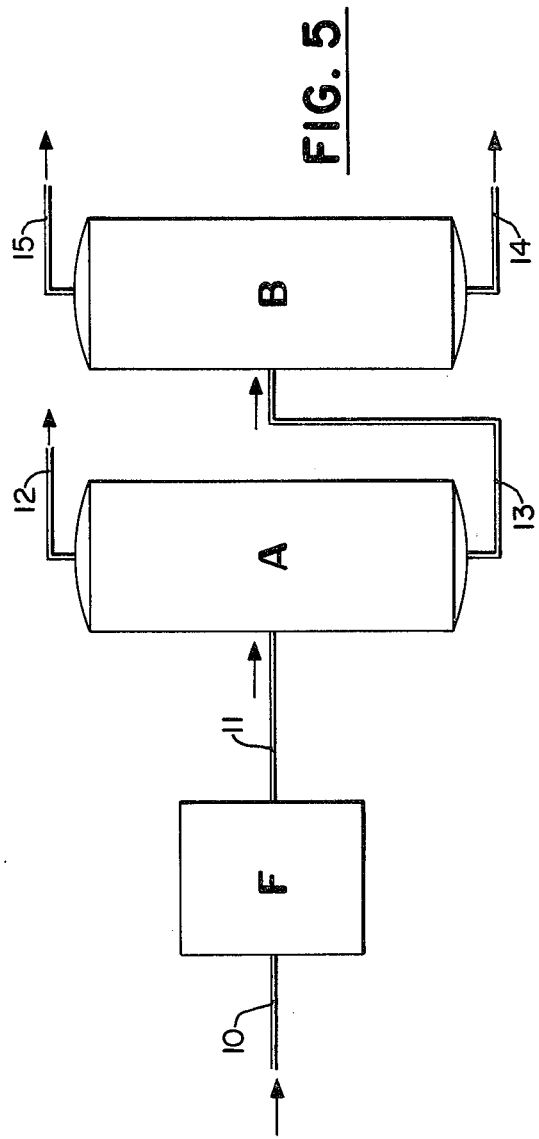

RECOVERY OF ISOPRENE

This invention relates to the recovery of isoprene from hydrocarbon streams consisting wholly or predominately of hydrocarbons containing five carbon atoms hereafter referred to as C-5 hydrocarbons. Hydrocarbon streams containing mostly C-5 hydrocarbons result from the steam cracking of naphtha and other hydrocarbon feed stocks primarily for the production of ethylene. These by-product C-5 streams contain sufficient isoprene to make them particularly suitable for recovery of isoprene.

Recent developments in polymer chemistry have made isoprene a desirable commodity. Catalyst systems have been discovered which when used in the solution polymerization of isoprene, cause isoprene to form a polyisoprene having stereo specific structures. Of particular interest is a polyisoprene in which the isoprene units are joined in a manner to produce a polyisoprene containing a high percentage somewhat above 90 percent of the isoprene units in a cis-1,4 configuration, by the use of catalyst comprising a mixture of aluminum trialkyl compound and titanium tetrachloride. This high cis-1,4-polyisoprene is particularly suitable as a replacement for natural rubber in such things as tires and other rubber products.

The prior art describes many methods for the synthetic preparation of isoprene or the recovery of isoprene from such by-product streams mentioned above.

For instance, in British Pat. No. 1,255,578, there is described a synethetic process for the production of isoprene wherein isobutylene is reacted or condensed with formaldehyde in the vapor phase while in the presence of a solid acid catalyst comprising silicon oxide and antimony oxide.

Still other methods have been suggested to separate or recover the isoprene contained in hydrocarbon streams rich in isoprene, such as, the hydrocarbon streams resulting from the steam cracking of naphtha. For instance, in U.S. Pat. No. 3,692,861, a highly pure isoprene is separated from a C-5 hydrocarbon fraction derived from the cracking of petroleum, particularly naphtha. Said stream containing C-5 paraffins, C-5 monoolefins, C-5 diolefins (isoprene), C-5 acetylenes and small amounts of other C-5 and C-6 hydrocarbons and sulphur where a major portion of the cyclopentadiene and acetylenes are removed by dimerizing by heat soaking and distillation and treating the remaining fraction with sodium dispersed in aliphatic monohydric alcohols having 1 to 18 carbon atoms. In U.S. Pat. No. 2,971,036, there is described a process for the separation of purified isoprene from a steam cracked C-5 fraction containing monoolefins and diolefins including isoprene and cyclopentadiene which comprises heat soaking said hydrocarbon fraction to dimerize a substantial amount of cyclopentadiene and then selectively distilling an isoprene rich fraction from the heat soaked fraction, separating the isoprene, the monoolefins and paraffins by extractive distillation with a solvent to extract the isoprene and cyclopentadiene, separating an isoprene concentrate and next heat soaking said concentrate in a second zone to dimerize the remaining cyclopentadiene, then distilling the isoprene from the heat soaked fraction. In U.S. Pat. No. 3,301,915 there is disclosed a process for the recovery of an isoprene fraction as an overhead by fractional distillation from a hydrocarbon stream containing isoprene and cyclopentadiene and consisting predominately of C-5 hydrocarbons, in which process, liquid is withdrawn during the course of the fractional distillation at in intermediate point in the distillation system and subjected to dimerization conditions to dimerize the cyclopentadiene and return this fraction to an intermediate point in the fractional distillation system. In British Pat. No. 1,225,549, there is described a process for the separation of isoprene from a C-5 hydrocarbon feed containing cyclopentadiene and acetylenes which comprises subjecting said C-5 stream to a first extractive distillation thereby removing a major proportion of the cyclopentadiene and acetylene and subjecting the remainder of the feed from the first extractive distillation to a second extractive distillation thereby selectively extracting an isoprene rich feed and subjecting this isoprene rich stream to two distillation processes.

All of these prior art methods have some disadvantage. The main disadvantage encountered with the prior art methods utilizing C-5 hydrocarbon streams containing isoprene is that entirely too many manipulative steps are used, such as, heat soaking, extractive distillations and double fractionations to remove the paraffinic hydrocarbons and the monoolefinic hydrocarbons from the isoprene. Other disadvantages in the prior art processes in which C-5 isoprene containing streams are used as the starting material is that long times and extra equipment is required for the recovery of isoprene. The main disadvantage of all of these prior art processes is that they require either large expenditures of capital for equipment and/or require substantial energy inputs of the use of heat for the multiple distillations and the like.

In the present invention, many of these disadvantages are overcome.

According to the present invention, isoprene meeting the monomer specifications for polymerization to high cis-1,4-polyisoprene is recovered from a hydrocarbon stream consisting of predominately C-5 hydrocarbons and containing isoprene, n-pentane and other 5 carbon atom hydrocarbons which comprises subjecting said hydrocarbon stream to two successive high efficiency distillations, the first distillation being conducted in a manner as to remove as an overhead fraction, hydrocarbon components of said stream which are more volatile than the azeotrope of isoprene/n-pentane and as a bottom fraction the other hydrocarbons in said stream, subjecting the bottom fraction from the first distillation to the second distillation, the second distillation being conducted in a manner as to remove the azeotrope of isoprene/n-pentane as an overhead fraction and as a bottom fraction the other hydrocarbons which are less volatile than the azeotrope of isoprene/n-pentane, and recovering the isoprene/n-pentane azeotrope.

It is known that feed stocks which result from the steam cracking of naphtha contain a number of hydrocarbon fractions. The fraction which is wholly or predominately composed of hydrocarbons containing 5 carbon atoms usually contains between about 8 and about 20 percent by weight of isoprene, from about 12 to about 30 percent by weight of pentenes, from about 6 to about 14 percent by weight of piperylene, from about 4 to about 20 percent by weight of 1,3-cyclopentadiene, about 0.01 to about 0.6 percent of various acetylenes, about 9 to about 20 percent by weight of isopentane, about 10 to about 20 percent of normal pentane and from about 2 to about 10 percent cyclopentane.

It is generally known that in the processes for the polymerization of isoprene to form high cis-1,4 polyisoprene by means of coordination catalyst particularly mixtures of aluminum trialkyl compounds and titanium tetrachloride that the polymerization mixture should be relatively free of cyclopentadiene and acetylenes as excessive amounts of these materials tend to act as poisons of such polymerization catalysts. Because of the binary azeotrope which exists between isoprene and n-pentane and the binary azeotropes which exist between n-pentane and various catalyst poisons including 1,3-cyclopentadiene and various acetylenes, it has always been considered impossible to recover polymerization grade isoprene directly by distillation without first removing the n-pentane from the stream by such means as an extractive distillation with a polar solvent. It has been discovered, however, that by subjecting a C-5 stream containing these components to a very high efficiency distillation the isoprene/n-pentane azeotropic mixture can be recovered essentially free of the catalyst poisons. The present invention provides a process whereby the isoprene values found in these crude C-5 streams can be removed from the other undesirable hydrocarbons particularly cyclopentadiene and acetylenes. Although various solvents are used in the polymerization, the purified n-pentane which is recovered with the isoprene is very useful and desirable as a polymerization solvent for the isoprene.

Typically, the process treats the isoprene/n-pentane azeotrope as a pure hydrocarbon rather than a mixture of two hydrocarbons. The azeotropic mixture contains about 73.4 weight percent isoprene and 26.6 weight percent n-pentane. For instance, a crude C-5 stream containing predominately isopentane, 1-pentene, 2-methyl-1-butene, isoprene, n-pentane, 2-methyl-2-butene, 1 trans-3-pentadiene, 1-cis-3-pentadiene, some cyclopentene, some cyclopentane, some 2-methyl-pentane, some 1,4-pentadiene and some 1,3-cyclopentadiene and some 3-methyl-1-butene along with small amounts of various acetylenic compounds is subjected to a first distillation step in which the hydrocarbons present which are more volatile than the azeotrope of isoprene/n-pentane are removed. The overhead fraction contains predominately isopentane, 1-pentene, 2-methyl-1-butene, a very small amount of isoprene, 3-methyl-1-butene and 1,4-pentadiene as well as small amounts of various other saturated and unsaturated C-4 and C-5 hydrocarbons, particularly acetylenes. This overhead fraction from the first distillation can be disposed of as gasoline as most, it not all, of the n-pentane has been removed and thus the raffinate is improved in octane value. The bottoms from this first distillation which contain predominately isoprene, n-pentane, 1,3-pentadiene, cyclopentene, trans-2-pentene, cis-2-pentene, 2-methyl-2-butene, 1,3-cyclopentadiene, cyclopentane, dicyclopentadiene and other hydrocarbons including other C-5 acetylenes are then subjected to a second distillation. In this second distillation, the azeotropic mixture of isoprene/n-pentane is taken overhead in amounts of about 73 percent by weight of isoprene and about 27 percent by weight of n-pentane. Sometimes minute amounts, usually less than 30 parts per million, of 1,3-cyclopentadiene, isopryne (2-methyl-1-butene-3-yne), 2-butyne, 1-pentyne and 1-penten-4-yne accompany the isoprene/n-pentane azeotrope. Because of the nature of the separation being discussed (the separation of isoprene/n-pentane azeotrope from excess n-pentane), the composition of the overhead would approach the composition of the azeotrope from the n-pentane rich side. The highest purity for a given column operation would result from an overhead composition approaching the azeotrope composition, however. The bottoms from this second distillation which consists primarily of n-pentane, trans-2-pentene, 2-methyl-2-butene, 2-methylpentene, 1,3-pentadiene and hexane as well as small amounts of other C-5 hydrocarbons and any dimerized 1,3-cyclopentadiene which are less volatile than the azeotrope can be disposed of economically by several methods. The bottoms from the second distillation can be a hydrocarbon resin feed stock, used in other elastomeric productions, hydrogenated and sold as gasoline blend feed stock or they may be burned and utilized as fuel. Thus, it can be seen that typically the invention consists of one of recovering the azeotropic mixture of isoprene/n-pentane, as well as other valuable hydrocarbon mixtures.

Distillation requirements for a given separation are not specific since many combinations of theoretical plates and reflux ratios will result in essentially the same separation. Also, differences in feed compositions affect the requirements for recovering a product of the same composition. In general, however, separating the isoprene/n-pentane azeotrope from a C-5 stream directly by distillation in a form suitable for polymerization (very low parts per million levels of 1,3-cyclopentadiene and acetylenes) would require 100 to 250 theoretical plates or trays. If greater than trace quantities of 1,3-cyclopentadiene and acetylenes could be tolerated because of a secondary removal method or a polymerization catalyst less sensitive than these poisons were to be used, the essentially pure azeotrope could be recovered in columns with fewer theoretical plates.

If one so desires, the small amounts of 1,3-cyclopentadiene in the azeotropic mixture of isoprene/n-pentane can be removed by subjecting the azeotropic mixture or overhead fraction from the second distillation step to a chemical treatment for the removal of the 1,3-cyclopentadiene. There are various chemical treatments known to remove cyclopentadiene from other hydrocarbon mixtures. For instance, it is known that the reaction between maleic anhydride and 1,3-cyclopentadiene will selectively allow the removal of cyclopentadiene from a mixture of hydrocarbons containing cyclopentadiene. One only has to treat the hydrocarbon stream containing the cyclopentadiene with maleic anhydride, or with maleic anhydride dissolved in a suitable solvent, which selectively forms an adduct with 1,3-cyclopentadiene which can be removed from the azeotrope by a flash distillation or by washing the mixture with a water solution of caustic.

Still another method which may be employed to remove the 1,3-cyclopentadiene is to treat the azeotropic mixture containing the 1,3-cyclopentadiene with sodium in the presence of an aliphatic alcohol. In this sodium treatment, it is usually desirable to have the sodium dispersed in an easily separatable hydrocarbon medium, usually in particle sizes from about 1 to about 100 microns. The dispersion usually contains about 20 to about 60 percent by weight of sodium. The aliphatic alcohols suitable for use in this process are methyl, ethyl, propyl, butyl, amyl, hexyl and the like. Of these, it is usually preferable to use isopropyl, isoamyl, tertiary butyl. The amount of sodium usually is based on the amount of 1,3-cyclopentadiene found in the hydrocarbon mixture and the amount of sodium to the amount of cyclopentadiene is about an equivalent amount or very slightly in excess.

If it is desirable to remove the trace amounts of acetylenes remaining in the azeotropic mixture of isoprene/n-pentane resulting from the distillation, a convenient method is the same method suggested above for cyclopentadiene, a treatment with sodium in the presence of an aliphatic alcohol. Thus, one could effect the removal of the 1,3-cyclopentadiene at the same time as the acetylenes are being removed by simply treating the azeotropic mixture of isoprene/n-pentane containing both 1,3-cyclopentadiene and acetylenes with sufficient sodium-alcohol mixture mentioned above to react with both the cyclopentadiene and the acetylenes simultaneously.

Still another method of removing the acetylenes selectively is to selectively hydrogenate the acetylenic impurities by passing the azeotrope along with hydrogen over a typical hydrogenation catalyst, such as, for instance, copper based catalyst primarily of copper on a silica support. Other hydrogenation catalysts which could be employed are cobalt/molybdena, palladium on alumina, palladium on copper-chromite or barium promoted copper-chromite.

Those skilled in the art can readily determine the conditions required for the maleic anhydride treatment, the sodium/alcohol treatment and the hydrogenation of the azeotropic mixture of isoprene/n-pentane to remove the 1,3-cyclopentadiene and/or the acetylenes from this azeotropic mixture, as these techniques are well known in the art.

There are a number of processing configurations which relate to the recovery of polymerization grade isoprene from C-5 streams as a mixture with n-pentane, primarily as the isoprene/n-pentane azeotrope. The choice of the preferred configuration would depend upon the source of C-5 hydrocarbons, the location of the various facilities and the desired purity of the isoprene.

The process of this invention will be further explained by making reference to the accompanying drawings. In these drawings, FIG. 1 which represents a preferred embodiment, A is the distillation column in which the first distillation is conducted so as to remove overhead from the distillation Column A, all the 5 carbon atom hydrocarbon components of the feed which are more volatile than the azeotrope of isoprene/n-pentane and B represents the second distillation tower which is operated so as to separate the excess n-pentane and all of the other 5 carbon atom hydrocarbons which are less volatile than the azeotrope and these hydrocarbons are discharged from Column B as bottoms and the azeotrope is discharged overhead from Column B.

If the purity requirements for isoprene were more moderate or if secondary treatments for removal of catalyst poisons such as 1,3-cyclopentadiene and acetylenes were desired for some reason, the configuration shown in FIG. 1 could be operated at reduced efficiency and an impure mixture of isoprene and n-pentane could be used directly or additional treatments could be used to achieve the desired purity.

In FIG. 2, which illustrates still another embodiment of the invention. Columns A and B are the same as described in FIG. 1 above and C is a Contactor wherein the azeotrope is contacted with maleic anhydride or other chemical treatment to remove 1,3-cyclopentadiene. This treatment with maleic anhydride causes a reaction with the 1,3-cyclopentadiene and the azeotrope is removed from these reaction products in Washer D as an overhead product, after being contacted with the water solution of caustic. An alternative method not shown of recovering the purified azeotrope from the maleic anhydride-cyclopentadiene adduct would be a simple flash distillation.

FIG. 4, which illustrates still another embodiment of the invention, Columns A and B are the same as described in FIG. 1 above and E is a hydrogenation unit for hydrogenation of acetylenic compounds if any, which are present in the azeotrope.

FIG. 3 illustrates still another embodiment of the invention wherein Columns A and B perform the same functions as they did in the embodiment of FIG. 1. The azeotrope mixture leaving Column B is further reacted with hydrogen while in the presence of a catalyst to hydrogenate the acetylenic compounds, if any, found in the azeotrope. After hydrogenation is complete, the azeotropic mixture may be contacted with maleic anhydride or other chemical treatment to remove 1,3-cyclopentadiene in C and the adduct of 1,3-cyclopentadiene and maleic anhydride washed out in Washer D or flash distilled in a stripping column not shown.

Because of the reactive nature of 1,3-cyclopentadiene which is found in concentrations up to 20 percent by weight in typical C-5 streams, it will readily dimerize to dicyclopentadiene. As indicated elsewhere, many known processes of purifying or recovering isoprene include the dimerization of cyclopentadiene to dicyclopentadiene which is generally referred to as heat soaking. The preferred embodiment of this invention has been demonstrated on C-5 streams containing up to 5 percent by weight of 1,3-cyclopentadiene. In order to assure the recovery of an isoprene/n-pentane azeotrope with very low levels of 1,3-cyclopentadiene, it may be desirable to reduce the concentrations of 1,3-cyclopentadiene in the feed to the embodiment illustrated by FIG. 1 to some concentration less than that found in a fresh C-5 stream from a naphtha steam cracker. It is highly possible that if this C-5 stream is stored for some period of time prior to the distillation to recover the isoprene, a significant amount of the cyclopentadiene will have dimerized. In any system of recovery of isoprene, including the configuration of FIG. 1, the first distillation Column or A can be designed to provide the heat soaking time necessary to dimerize a significant amount of the cyclopentadiene. In most designs, a column required to perform the operation provides sufficient time for dimerization without a significant change in operating conditions or column designs. This fact is an advantage of this invention since the requirements and expense for a separate heat soaking operation can be eliminated.

However, as an alternative to any of the embodiments which have been described above, and in the event that the C-5 stream did not require any substantial storage prior to the recovery of the isoprene, a preliminary heat soaking unit can be used to reduce the concentration of the cyclopentadiene of the feed stream. This approach is illustrated by FIG. 5 which is a modification of the embodiment of FIG. 1 in which F is simply a large holding tank wherein the C-5 stream containing a high percentage of cyclopentadiene is held at ambient temperature or higher for a sufficient period of time to dimerize a substantial amount of the cyclopentadiene to dicyclopentadiene which then can be disposed of at the bottom of Column B through line 14 along with the other hydrocarbons less volatile than the azeotrope. Columns A and B operate in the identical manner in FIG. 5 as they do in FIG. 1.

In the operation of the embodiment of FIG. 1, the crude mixed 5 carbon hydrocarbon stream enters Column A through inlet line 11. The hydrocarbon components more volatile than the azeotrope of isoprene/n-pentane exit Column A overhead through line 12 and are disposed of as previously indicated. The remaining components exit Column A through line 13 and enter Column B. In Column B, the excess n-pentane and all other components less volatile than the isoprene/n-pentane azeotrope exit Column B through line 14 and are disposed of as previously indicated. The azeotrope of isoprene/n-pentane is recovered from Column B overhead through line 15 for further use in the polymerization plant.

In the embodiment illustrated by FIG. 2, A and B function in the identical manner as that of FIG. 1; however, the azeotropic mixture enters Contactor C via line 15 and the maleic anhydride or maleic anhydride in a suitable solvent enters C via line 16. After the adduct of the maleic anhydride/cyclopentadiene is formed, the total mixture exits C via line 17 to Washer D where the adduct is washed out of the azeotrope or alternatively enters a flash distillation column, not shown, where the azeotrope is flashed from the adduct. In D the caustic water enters through line 22 and after contacting the mixture to remove the adduct from the azeotrope, the caustic water exits D via line 19 and is disposed of or recycled for further use. The azeotrope exits D via line 18 and is recovered for polymerization use later.

In the operation of the embodiment illustrated by FIG. 4, Columns A and B function in the same manner as that of FIG. 1. Column E is packed with a suitable hydrogenation catalyst. The isoprene/n-pentane azeotrope enters Column E through line 15. Hydrogen in an amount to hydrogenate the acetylenes which may be present in the azeotropic mixture enters Column E through line 20 and the azeotrope and the hydrogen are allowed to flow upward in Column E to hydrogenate the acetylenes in the azeotrope as a flooded bed hydrogenation. The azeotrope and the hydrogenated products of the acetylenes exit Column E through line 21 and is collected for further use in subsequent polymerization.

In the operation of the embodiment illustrated by FIG. 3, Columns A and B operate in the same manner as in the embodiment illustrated by FIG. 1. When the azeotrope exits Column B through line 15, it is passed onto Column E. Column E is packed with a suitable hydrogenation catalyst. Hydrogen enters Column E through line 20 and the azeotrope and hydrogen are allowed to flow upward in Column E to hydrogenate the acetylenes in the azeotrope in a flooded bed. The hydrogenated azeotrope exits Column E through line 21, and enters Contactor C. Contactor C and Washer D operate in the same manner as indicated in FIG. 2.

In the operation of the embodiment illustrated by FIG. 5, the feed stock consisting of C-5 hydrocarbons containing substantial amounts of 1,3-cyclopentadiene are fed to holding tank F through line 10. After sufficient time has elapsed to dimerize a substantial portion of the 1,3-cyclopentadiene to dicyclopentadiene, the mixture enters Column A through line 11. Columns A and B function from that point forward in the identical manner as they do in FIG. 1.

In any of the embodiments illustrated by FIGS. 1, 2, 3, 4 or 5, the purified azeotropic mixture of isoprene and n-pentane is then transferred to the polyisoprene plant. In the polyisoprene plant, the isoprene is polymerized to high cis-1,4-polyisoprene if it is desired to do so. A number of catalyst systems are known by which isoprene may be converted into high cis-1,4-polyisoprene usually as solution polymerizations. On the other hand, the isoprene exiting from the recovery operation can be employed for any other processes as it is a highly purified isoprene/n-pentane composition. The n-pentane in the isoprene mixture supplies the inert solvent in which the isoprene and polyisoprene is dissolved during the polymerization step.

After the isoprene has been polymerized, the n-pentane is recovered from the polymer recovery step and n-pentane can be sold for use as a solvent or it can be sold for use as a feed stream for steam cracking to produce ethylene. As has been previously discussed, the practice of the process of this invention divides up a C-5 fraction from steam cracking of naphtha into useful portions which may be used for gasoline blending, chemical uses, polyisoprene production or steam cracking feed stock. Thus, not only does this invention provide a unique and economical method for the recovery of polymerization grade isoprene, it also provides an excellent method to provide purified solvent for the solution polymerization of the isoprene. It also provides valuable by-products for gasoline and chemical uses and feeds to further cracking processes.

The practice of this invention will become further apparent with reference to the following examples. In these examples, all percentages are by weight unless otherwise stated. These examples are intended to be illustrative rather than restrictive of the scope of the invention. These distillations were carried out in the manner as indicated by FIG. 1.

EXAMPLE I

A mixed hydrocarbon stream containing predominately hydrocarbons of 5 carbon atoms resulting from the steam cracking of naphtha was distilled in two stages. In the first stage distillation, the column used was 3 inches by 36 feet equivalent to 118 theoretical plates. Hydrocarbons more volatile than the azeotropic mixture of isoprene/n-pentane were removed overhead. The bottoms were redistilled in the second stage distillation using a column similar to that used in the first stage distillation also equivalent to 118 theoretical plates where the azeotropic of isoprene/n-pentane was removed overhead from the excess normal pentane and other materials less volatile than the azeotropic mixture which were rejected as bottoms from the second stage distillation.

A typical C-5 hydrocarbon stream having the composition set forth below was fed to the first stage distillation column (Column A in FIG. 1) at a rate so that the overheads isoprene content only averaged about 3.2 percent by weight.

| Feed to First Stage | |
|---|---|
| Component | Weight Percent |
| 3-methyl-1-butyne | 0.004 |
| isopryne | 0.07 |
| 2-butyne | 0.48 |
| 3-methyl-1-butene | 0.44 |

-continued

| Feed to First Stage | |
|---|---|
| Component | Weight Percent |
| 1,4-pentadiene | 1.4 |
| isopentane | 11.7 |
| 1-pentene | 2.6 |
| 2-methyl-1-butene | 4.2 |
| isoprene | 15.2 |
| n-pentane | 19.4 |
| trans-2-pentene | 1.6 |
| cis-2-pentene | 0.8 |
| 2-methyl-2-butene | 2.5 |
| 1,3-cyclopentadiene | 5.3 |
| 2-methyl pentane | 3.0 |
| 1-trans-3-pentadiene | 6.1 |
| 3-methyl pentane | 1.1 |
| cyclopentene | 3.2 |
| 1-cis-3-pentadiene | 3.3 |
| cyclopentane | 3.3 |
| n-hexane | 1.3 |
| 1,5-hexadiene | 0.4 |
| 3-methyl-trans-2-pentene | 0.1 |
| benzene | 0.6 |
| heavies | 12.6 |

The column was operated for a period of approximately 16 days under the following conditions.

| | Range | Average |
|---|---|---|
| Overhead °C | 36.6–38.1 | 37.3 |
| Feed and Reflux °C | 33.8–38.1 | 36.1 |
| Bottom °C | 53.6–55.5 | 54.4 |
| Overhead Press (psig) | 7.19–7.35 | 7.29 |
| Column P, in H$_2$O | 29.2–35.9 | 32.8 |
| Average Reflux Ratio | | 100/1 |

The overheads from this first stage distillation had an average content as set forth below.

| First Stage Overheads | |
|---|---|
| Component | Weight Percent |
| 3-methyl-1-butyne | 0.01 |
| isopryne | 0.4 |
| 2-butyne | 2.1 |
| 3-methyl-1-butene | 2.0 |
| 1,4-pentadiene | 6.4 |
| isopentane | 52.2 |
| 1-pentene | 12.6 |
| 2-methyl-1-butene | 21.0 |
| isoprene | 3.2 |

The bottoms from the first stage distillation had an average composition as set forth below.

| First Stage Bottoms | |
|---|---|
| Component | Weight Percent |
| 2-methyl-1-butene | t |
| isoprene | 14.5 |
| n-pentane | 26.8 |
| trans-2-pentene | 2.9 |
| cis-2-pentene | 1.4 |
| 2-methyl-2-butene | 3.7 |
| 1,3-cyclopentadiene | 4.7 |
| 2-methyl pentane | 5.5 |
| 3- or 4-methyl-1-pentene | 0.2 |
| 1-trans-3-pentadiene | 5.6 |
| 3-methyl pentane | 1.9 |
| cyclopentene | 3.7 |
| 1-cis-3-pentadiene | 4.0 |
| cyclopentane | 2.6 |
| hexane | 1.8 |
| unknown | 0.3 |
| 1,5-hexadiene | 0.4 |
| 2,3-dimethyl-butane | 0.2 |
| 2-methyl-1-pentene | 0.5 |
| 2-pentyne | 0.2 |
| 3-methyl-trans-2-pentene | 0.2 |

| First Stage Bottoms | |
|---|---|
| Component | Weight Percent |
| benzene | 1.0 |
| heavies (primarily dicyclopentadiene) | 18.7 |

The bottoms from the first stage distillation was fed to the second stage column (Column B of FIG. 1) at a rate so that the isoprene content rejected in the bottoms averaged only 1.1 percent.

The column was operated under the following conditions for approximately 12 days.

| | Range | Average |
|---|---|---|
| Overhead °C | 42.6–44.0 | 43.3 |
| Feed and Reflux °C | 34.3–38.3 | 36.2 |
| Bottom °C | 65.0–77.6 | 73.0 |
| Overhead Press (psig) | 7.30–7.48 | 7.41 |
| Column P, in H$_2$O | 29.9–36.7 | 33.4 |
| Average Reflux Ratio | | 100/1 |

The second stage distillation produced an overhead which consisted predominately of the azeotrope of isoprene/n-pentane and had an average composition as set forth below, which is suitable for polymerization to polyisoprene by the use of a catalyst such as a mixture of aluminum trialkyl compounds and titanium tetrachloride.

| Second Stage Overheads | | |
|---|---|---|
| Component | Weight Percent | |
| 1-pentyne | 0.1 | ppm |
| isopryne | < 2.0 | ppm |
| 2-butyne | <10 | ppm |
| 2-methyl-1-butene | 0.04 | |
| isoprene | 74.02 | |
| n-pentane | 25.91 | |
| 1,3-cyclopentadiene | < 2.0 | ppm |
| 1-penten-4-yne | 33.0 | ppm |

The second stage bottoms which were rejected had an average composition as set forth below.

| Second Stage Bottoms | |
|---|---|
| Component | Weight Percent |
| isoprene | 1.1 |
| n-pentane | 23.2 |
| trans-2-pentene | 3.4 |
| cis-2-pentene | 1.7 |
| 2-methyl-2-butene | 4.4 |
| 1,3-cyclopentadiene | 2.5 |
| 2-methyl pentane | 6.2 |
| 3- or 4-methyl-1-pentene | 0.3 |
| 1-trans-3-pentadiene | 8.4 |
| 3-methyl pentane | 2.5 |
| cyclopentene | 5.9 |
| 1-cis-3-pentadiene | 5.8 |
| cyclopentane | 3.4 |
| n-hexane | 2.2 |
| 2,3-dimethyl-butane | 0.2 |
| 2-methyl-1-pentene | 1.0 |
| 2-pentyne | 0.1 |
| 3-methyl-trans-2-pentene | 0.1 |
| benzene | 1.0 |
| heavies (primarily dicyclopentadiene) | 28.6 |

EXAMPLE II

A mixed hydrocarbon stream containing predominately hydrocarbons of five carbon atoms resulting from the steam cracking of naphtha was distilled in two steps or stages in a distillation column similar to that employed in the first distillation of Example I. The materials boiling lower than the azeotrope of isoprene/n-pentane was removed overhead in the first column. The bottoms from the first column were distilled in a second stage distillation again using a column similar to that employed in the second distillation of Example I in which the azeotrope of isoprene/n-pentane was removed overhead from the excess n-pentane and other materials boiling higher than the azeotrope which materials were removed as the bottoms of the second stage distillation.

A typical C-5 hydrocarbon stream having a composition set forth below was fed to the first stage distillation column at a rate so that the light ends overhead isoprene content averaged about 8.7 percent

| Feed to First Stage Component | Weight Percent |
|---|---|
| 1-butene | 0.2 |
| 3-methyl-1-butyne | 25 ppm |
| isopryne | 0.1 |
| 2-butyne | 0.4 |
| 3-methyl-1-butene | 1.5 |
| trans-2-butene | 0.1 |
| 1,4-pentadiene | 1.9 |
| cis-2-butene | 0.2 |
| 1,3-butadiene | 0.2 |
| isopentane | 8.8 |
| 1-pentene | 5.8 |
| 2-methyl-1-butene | 6.9 |
| isoprene | 17.5 |
| n-pentane | 13.9 |
| trans-2-pentene | 4.2 |
| cis-2-pentene | 2.0 |
| 2-methyl-2-butene | 4.1 |
| 1,3-cyclopentadiene | 2.4 |
| 2-methyl pentane | 2.1 |
| 3- or 4-methyl-1-pentene | 0.2 |
| 1,trans-3-pentadiene | 7.3 |
| 3-methyl pentane | 0.6 |
| cyclopentene | 3.0 |
| 1,cis-3-pentadiene | 4.7 |
| cyclopentane | 1.3 |
| n-hexane | 0.7 |
| 1,5-hexadiene | 0.2 |
| 2,3-dimethyl butane | 0.2 |
| 2-methyl-1-pentene | 0.4 |
| 2-pentyne | 0.05 |
| benzene | 0.4 |
| heavies | 8.9 |

The column was operated for a period of approximately 14 days under the following conditions.

| | Range | Average |
|---|---|---|
| Overheads, °C | 35.6–38.7 | 37.6 |
| Feed and Reflux, °C | 33.1–37.0 | 35.3 |
| Bottom, °C | 54.6–62.4 | 60.1 |
| Overhead Pressure, psig | 7.04–7.43 | 7.32 |
| Column 2ΔP, in H₂O | 28.1–37.5 | 32.5 |
| Average Reflux Ratio | | 100/1 |

The overhead from this first stage distillation had an average composition set forth below.

| First Stage Overhead Component | Weight Percent |
|---|---|
| isobutylene | 0.3 |
| 1-butyne | 0.3 |
| 3-methyl-1-butyne | 0.02 |
| isopryne | 0.3 |
| 2-butyne | 1.5 |
| 3-methyl-1-butene | 5.1 |
| trans-2-butene | 0.2 |
| 1,4-pentadiene | 7.2 |
| cis-2-butene | 0.6 |
| 1,3-butadiene | 0.1 |
| isopentane | 29.4 |
| 1-pentene | 20.3 |
| 1,2-butadiene | 0.7 |
| 2-methyl-1-butene | 25.4 |
| isoprene | 8.7 |
| n-pentane | trace |

The bottoms from this first stage distillation had a composition as set forth below.

| First Stage Bottoms Component | Weight Percent |
|---|---|
| isoprene | 22.1 |
| n-pentane | 17.0 |
| trans-2-pentene | 5.8 |
| cis-2-pentene | 3.4 |
| 2-methyl-2-butene | 5.3 |
| 1,3-cyclopentadiene | 1.8 |
| 2-methylpentane | 3.0 |
| 3- or 4-methyl-1-pentene | 0.2 |
| 1,trans-3-pentadiene | 10.2 |
| 3-methyl pentane | 1.2 |
| cyclopentane | 4.6 |
| 1,cis-3-pentadiene | 6.1 |
| cyclopentene | 2.0 |
| unknown | 0.5 |
| n-hexane | 1.0 |
| 1,5-hexadiene | 0.2 |
| 2,3-dimethyl butane | 0.1 |
| 2-pentyne | 0.1 |
| benzene | 0.5 |
| 3-methyl-trans-2-pentene | 0.1 |
| heavies (primarily dicyclopentadiene) | 14.6 |

The bottoms from the first stage distillation was fed to the second distillation column at a rate so that the isoprene content rejected in the bottoms averaged 1.5 percent. This column was operated under the following conditions for approximately 7 days.

| | Range | Average |
|---|---|---|
| Overhead, °C | 42.9–45.0 | 43.5 |
| Feed and Reflux, °C | 33.6–38.6 | 35.8 |
| Bottom, °C | 65.5–75.6 | 71.1 |
| Overhead Pressure, psig | 7.05–7.34 | 7.29 |
| Column 2 P, in H₂O | 29.8–37.5 | 33.7 |
| Average Reflux Ratio | | 100/1 |

The second stage distillation produced an overhead which consisted predominately of the azeotropic mixture of isoprene/n-pentane and had an average composition as follows which is suitable for polymerization to polyisoprene by catalyst such as a mixture of an aluminum trialkyl compound and titanium tetrachloride.

| Second Stage Overhead Component | Weight Percent | |
|---|---|---|
| 1-pentyne | 0.1 | ppm |
| isopryne | 2 | ppm |
| 2-butyne | 10 | ppm |
| 2-methyl-1-butene | 0.05 | |
| isoprene | 73.30 | |
| n-pentane | 26.61 | |
| 1,3-cyclopentadiene | 2 | ppm |
| 1-pentene-4-yne | 126 | ppm |

The second stage bottoms which were rejected had an average composition as set forth below.

| Component | Second Stage Bottoms Weight Percent |
| --- | --- |
| isoprene | 1.5 |
| n-pentane | 11.9 |
| trans-2-pentene | 8.5 |
| cis-2-pentene | 5.2 |
| 2-methyl-2-butene | 8.4 |
| 1,3-cyclopentadiene | 2.2 |
| 2-methylpentane | 4.5 |
| 3- or 4-methyl-1-pentene | 0.4 |
| 1,trans-3-pentadiene | 16.6 |
| cyclopentene | 7.1 |
| 3-methylpentane | 1.8 |
| 1,cis-3-pentadiene | 9.8 |
| cyclopentane | 3.1 |
| unknown | 0.8 |
| n-hexane | 1.4 |
| 1,5-hexadiene | 0.4 |
| 2,3-dimethyl butane | 0.1 |
| 2-pentyne | 0.1 |
| benzene | 0.7 |
| 3-methyl-trans-2-pentene | 0.1 |
| heavies (primarily dicyclopentadiene) | 15.0 |

It has been demonstrated experimentally that polymerization grade isoprene can be recovered directly by distillation from C-5 streams in the form of isoprene/n-pentane azeotrope. The number of theoretical plates required is high, but the distillation requirements are comparable with those for isoprene streams of the same purity without n-pentane present. The distillations which were performed experimentally are equivalent to approximately 200 theoretical plates at a reflux ratio of 30/1.

Thus, the invention is a method of recovery of isoprene from a hydrocarbon stream consisting of predominately C-5 hydrocarbons and containing isoprene, n-pentane and other 5 carbon atom hydrocarbons which comprises subjecting said hydrocarbon stream to two successive high efficiency distillations, the first distillation being conducted in a manner as to remove as an overhead fraction, hydrocarbon components of said stream which are more volatile than the azeotrope of isoprene/n-pentane and as a bottom fraction the other hydrocarbons in the said stream, subjecting the bottom fraction from the first distillation to the second distillation, the second distillation being conducted in a manner as to remove the azeotrope of isoprene/n-pentane as an overhead fraction and as a bottom fraction the other hydrocarbons which are less volatile than the azeotrope of isoprene/n-pentane, and recovering the isoprene/n-pentane azeotrope.

The invention also includes as an embodiment the method above in which the isoprene/n-pentane azeotrope is subjected to a chemical treatment to remove 1,3-cyclopentadiene present. It also includes the embodiment of the method above in which the azeotrope of isoprene/n-pentane is subjected to hydrogenation to remove acetylenes present. It also includes the embodiment of the method above wherein the azeotrope is subject to both the chemical treatment and hydrogenation. It also includes the concept of taking overhead in the second distillation of the method above excess n-pentane along with the azeotrope.

While certain representative embodiments and details have been shown for the purpose of illustrating the invention, it will be apparent to those skilled in this art that various changes and modifications may be made therein without departing from the spirit or scope of the invention.

What is claimed is:

1. A method of recovery of isoprene from a hydrocarbon stream of predominately C-5 hydrocarbons and containing isoprene, n-pentane and other 5 carbon atom hydrocarbons which comprises subjecting said hydrocarbon stream to two successive high efficiency distillations, the first distillation being conducted in a manner as to remove as an overhead fraction, hydrocarbon components of said stream which are more volatile than the azeotrope of isoprene/n-pentane and as a bottom fraction the other hydrocarbons in said stream, subjecting the bottom fraction from the first distillation to the second distillation, the second distillation being conducted in a manner as to remove a composition containing about 73.4 weight percent isoprene and about 26.6 weight percent n-pentane, the azeotrope of isoprene/n-pentane as an overhead fraction and as a bottom fraction the other hydrocarbons which are less volatile than the azeotrope of isoprene/n-pentane, and recovering the isoprene/n-pentane azeotrope.

2. A method according to claim 1 in which the isoprene/n-pentane is subjected to a chemical treatment to remove 1,3-cyclopentadiene present.

3. The method according to claim 1 in which the azeotrope of isoprene/n-pentane is subjected to hydrogenation to remove acetylenes present.

4. The method according to claim 1 in which the isoprene/n-pentane azeotrope is subjected to hydrogenation to remove acetylenes and the hydrogenated isoprene/n-pentane azeotrope is subjected to a chemical treatment to remove 1,3-cyclopentadiene.

* * * * *